US012569224B2

(12) United States Patent
Butler

(10) Patent No.: US 12,569,224 B2
(45) Date of Patent: Mar. 10, 2026

(54) INTRAVASCULAR IMAGING DEVICES

(71) Applicant: BOSTON SCIENTIFIC SCIMED, INC., Maple Grove, MN (US)

(72) Inventor: Quinn Mackenzie Butler, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 88 days.

(21) Appl. No.: 18/143,836

(22) Filed: May 5, 2023

(65) Prior Publication Data

US 2023/0355206 A1     Nov. 9, 2023

Related U.S. Application Data

(60) Provisional application No. 63/339,159, filed on May 6, 2022.

(51) Int. Cl.
*A61B 8/00*          (2006.01)
*A61B 5/00*          (2006.01)
(Continued)

(52) U.S. Cl.
CPC ............ *A61B 8/445* (2013.01); *A61B 5/0066* (2013.01); *A61B 5/0084* (2013.01);
(Continued)

(58) Field of Classification Search
CPC ..... A61B 8/445; A61B 5/0066; A61B 5/0084; A61B 8/0891; A61M 25/0032;
(Continued)

(56) References Cited

U.S. PATENT DOCUMENTS

| | | | |
|---|---|---|---|
| 4,841,977 A | 6/1989 | Griffith et al. | |
| 5,375,602 A | 12/1994 | Lancee et al. | |
| | (Continued) | | |

FOREIGN PATENT DOCUMENTS

| | | | |
|---|---|---|---|
| CN | 109044404 A | 12/2018 | |
| EP | 2679167 A1 | 1/2014 | |
| | (Continued) | | |

OTHER PUBLICATIONS

International Search Report and Written Opinion dated Dec. 19, 2018 for International Application No. PCT/US2018/052685.
(Continued)

*Primary Examiner* — Sean A Frith
(74) *Attorney, Agent, or Firm* — Seager, Tufte & Wickhem, LLP

(57)                    ABSTRACT

Intravascular imaging devices and methods for making and using intravascular imaging devices are disclosed. An example intravascular imaging device may include a catheter shaft assembly including a telescoping assembly and a catheter body. The catheter body may include an imaging window and a distal end region having a first guidewire lumen formed therein. An imaging core may be disposed within the catheter shaft assembly. A distal shaft member may be disposed along an outer surface of the catheter body. The distal shaft member may have a second guidewire lumen formed therein. The intravascular imaging device may also include rod having a first end region coupled to the distal shaft member and a second end region coupled to the telescoping assembly.

17 Claims, 9 Drawing Sheets

(51) Int. Cl.

| | | |
|---|---|---|
| *A61B 8/08* | (2006.01) | |
| *A61M 25/00* | (2006.01) | |
| *A61M 25/01* | (2006.01) | |
| *A61M 25/09* | (2006.01) | |

(52) U.S. Cl.

CPC ... *A61B 8/0891* (2013.01); *A61M 2025/0004* (2013.01); *A61M 25/0032* (2013.01); *A61M 2025/0037* (2013.01); *A61M 2025/0177* (2013.01); *A61M 25/09* (2013.01)

(58) Field of Classification Search

CPC .......... A61M 25/09; A61M 2025/0004; A61M 2025/0037; A61M 2025/0177

See application file for complete search history.

(56) References Cited

U.S. PATENT DOCUMENTS

| | | | |
|---|---|---|---|
| 5,643,297 | A | 7/1997 | Nordgren et al. |
| 5,658,309 | A * | 8/1997 | Berthiaume ...... A61M 25/0097 |
| | | | 606/192 |
| 5,993,460 | A * | 11/1999 | Beitelia ................... A61F 2/958 |
| | | | 623/1.11 |
| 6,004,271 | A | 12/1999 | Moore |
| 6,292,681 | B1 | 9/2001 | Moore |
| 6,482,171 | B1 * | 11/2002 | Corvi ................. A61M 1/3659 |
| | | | 156/175 |
| 6,945,938 | B2 | 9/2005 | Grunwald |
| 6,966,891 | B2 | 11/2005 | Ookubo et al. |
| 7,037,271 | B2 | 5/2006 | Crowley |
| 7,246,959 | B2 | 7/2007 | Nakatani |
| 7,306,561 | B2 | 12/2007 | Sathyanarayana |
| 7,622,853 | B2 | 11/2009 | Rehrig et al. |
| 7,625,367 | B2 | 12/2009 | Adams et al. |
| 7,666,143 | B2 | 2/2010 | Wilser et al. |
| 8,062,226 | B2 | 11/2011 | Moore |
| 8,114,032 | B2 | 2/2012 | Ferry et al. |
| 8,147,414 | B2 | 4/2012 | Abraham |
| 8,317,711 | B2 | 11/2012 | Dala-Krishna |
| 8,323,203 | B2 | 12/2012 | Thornton |
| 8,403,856 | B2 | 3/2013 | Corl |
| 8,523,778 | B2 | 9/2013 | Sadaka |
| 9,084,575 | B2 | 7/2015 | Moore et al. |
| 9,839,410 | B2 | 12/2017 | Courtney et al. |
| 9,872,665 | B2 | 1/2018 | Okubo et al. |
| 9,895,163 | B2 | 2/2018 | Trovato |
| 9,931,101 | B2 | 4/2018 | Okubo et al. |
| 10,039,522 | B2 | 8/2018 | Magnin et al. |
| 10,052,082 | B2 | 8/2018 | Oliver et al. |
| 10,076,272 | B2 | 9/2018 | Devgon et al. |
| 10,130,337 | B2 | 11/2018 | Okubo et al. |
| 10,130,427 | B2 | 11/2018 | Tanner et al. |
| 10,143,411 | B2 | 12/2018 | Cabot |
| 10,204,718 | B2 | 2/2019 | Williams et al. |
| 10,420,456 | B2 | 9/2019 | Zelenka et al. |
| 10,420,530 | B2 | 9/2019 | Hancock et al. |
| 10,448,922 | B2 | 10/2019 | Van Hoven et al. |
| 10,485,608 | B2 | 11/2019 | Moisa et al. |
| 10,492,757 | B2 | 12/2019 | Sakaguchi |
| 10,555,780 | B2 | 2/2020 | Tanner et al. |
| 10,575,819 | B2 | 3/2020 | Davies et al. |
| 10,758,207 | B2 | 9/2020 | Park et al. |
| 10,779,796 | B2 | 9/2020 | Hiltner et al. |
| 10,905,851 | B2 | 2/2021 | Zelenka et al. |
| 10,932,752 | B2 | 3/2021 | Sakaguchi |
| 10,993,694 | B2 | 5/2021 | Meyer et al. |
| 11,076,829 | B2 | 8/2021 | Okubo et al. |
| 11,213,356 | B2 | 1/2022 | Tanner et al. |
| 2003/0097072 | A1 | 5/2003 | Serrano et al. |
| 2004/0108789 | A1 | 6/2004 | Marshall |
| 2004/0181174 | A2 | 9/2004 | Davis et al. |
| 2005/0124857 | A1 | 6/2005 | Adams et al. |
| 2005/0143664 | A1 | 6/2005 | Chen et al. |
| 2006/0058622 | A1 | 3/2006 | Tearney et al. |
| 2006/0084875 | A1 | 4/2006 | Knight |
| 2006/0100522 | A1 | 5/2006 | Yuan et al. |
| 2006/0106320 | A1 | 5/2006 | Barbato |
| 2006/0173350 | A1 | 8/2006 | Yuan et al. |
| 2006/0253028 | A1 | 11/2006 | Lam et al. |
| 2007/0016054 | A1 | 1/2007 | Cao et al. |
| 2007/0038111 | A1 | 2/2007 | Rehrig et al. |
| 2007/0083119 | A1 | 4/2007 | Adachi et al. |
| 2007/0167827 | A1 | 7/2007 | Masters |
| 2009/0156941 | A1 | 6/2009 | Moore |
| 2009/0163817 | A1 | 6/2009 | Masters et al. |
| 2009/0264769 | A1 | 10/2009 | Sadaka |
| 2009/0270737 | A1 | 10/2009 | Thornton |
| 2010/0249603 | A1 | 9/2010 | Hastings et al. |
| 2011/0071400 | A1 | 3/2011 | Hastings et al. |
| 2011/0098573 | A1 | 4/2011 | Thornton et al. |
| 2011/0207995 | A1 | 8/2011 | Snow et al. |
| 2012/0059241 | A1 | 3/2012 | Hastings et al. |
| 2012/0197113 | A1 | 8/2012 | Courtney et al. |
| 2012/0253197 | A1 | 10/2012 | Sadaka |
| 2013/0079642 | A1 | 3/2013 | Marshall et al. |
| 2013/0216114 | A1 | 8/2013 | Courtney et al. |
| 2014/0031797 | A1 | 1/2014 | Cohen et al. |
| 2014/0171804 | A1 | 6/2014 | Van Hoven |
| 2014/0180127 | A1 | 6/2014 | Meyer et al. |
| 2015/0196285 | A1 | 7/2015 | Mori |
| 2015/0359510 | A1 | 12/2015 | Currlin et al. |
| 2016/0324503 | A1 * | 11/2016 | Norris ...................... A61B 8/12 |
| 2017/0164925 | A1 | 6/2017 | Marshall et al. |
| 2017/0333000 | A1 * | 11/2017 | Nystrom ................ A61B 8/445 |
| 2018/0146948 | A1 * | 5/2018 | Chou ..................... A61B 8/466 |
| 2018/0280680 | A1 | 10/2018 | Isaacson et al. |
| 2018/0368934 | A1 | 12/2018 | Van Der Linde et al. |
| 2019/0151128 | A1 | 5/2019 | Cohen et al. |
| 2019/0357879 | A1 | 11/2019 | Cor |
| 2020/0086086 | A1 | 3/2020 | Barone et al. |
| 2020/0100764 | A1 | 4/2020 | Sakaguchi |
| 2020/0129149 | A1 | 4/2020 | Tokida et al. |
| 2020/0187904 | A1 | 6/2020 | Davies et al. |
| 2020/0275909 | A1 | 9/2020 | Winiece et al. |
| 2021/0128109 | A1 | 5/2021 | Groenland et al. |
| 2021/0298718 | A1 | 9/2021 | Saroha et al. |
| 2021/0338199 | A1 | 11/2021 | Sakaguchi |
| 2022/0015740 | A1 | 1/2022 | Sakaguchi |

FOREIGN PATENT DOCUMENTS

| | | | |
|---|---|---|---|
| EP | 2832295 | A1 | 2/2015 |
| JP | 2005177205 | A | 7/2005 |
| JP | 20110152274 | A | 8/2011 |
| JP | 5797195 | B2 | 10/2015 |
| JP | 2019217298 | A | 12/2019 |
| JP | 6913703 | B2 | 8/2021 |
| WO | 9956627 | A1 | 11/1999 |
| WO | 2005056096 | A1 | 6/2005 |
| WO | 2009048339 | A1 | 4/2009 |
| WO | 2009073752 | A1 | 6/2009 |
| WO | 2009079569 | A2 | 6/2009 |
| WO | 2009108863 | A1 | 9/2009 |
| WO | 2009121067 | A1 | 10/2009 |
| WO | 2014100606 | A1 | 6/2014 |

OTHER PUBLICATIONS

International Search Report and Written Opinion dated Jun. 16, 2023 for International Application No. PCT/US2023/015502.

International Search Report and Written Opinion dated Aug. 3, 2023 for International Application No. PCT/US2023/021155.

International Search Report and Written Opinion dated Jul. 17, 2023 for International Application No. PCT/US2023/016738.

* cited by examiner

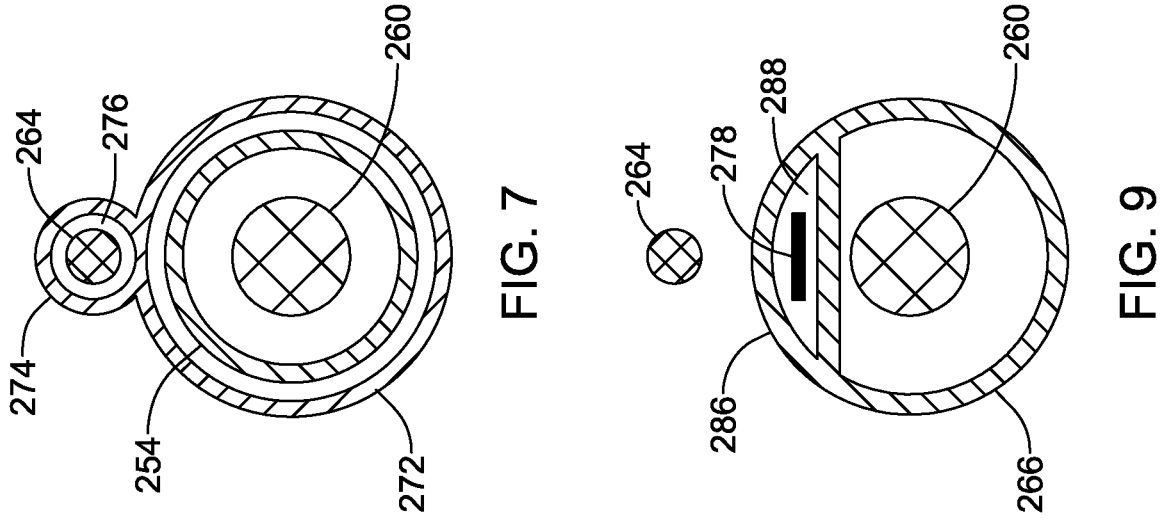
FIG. 6
FIG. 7
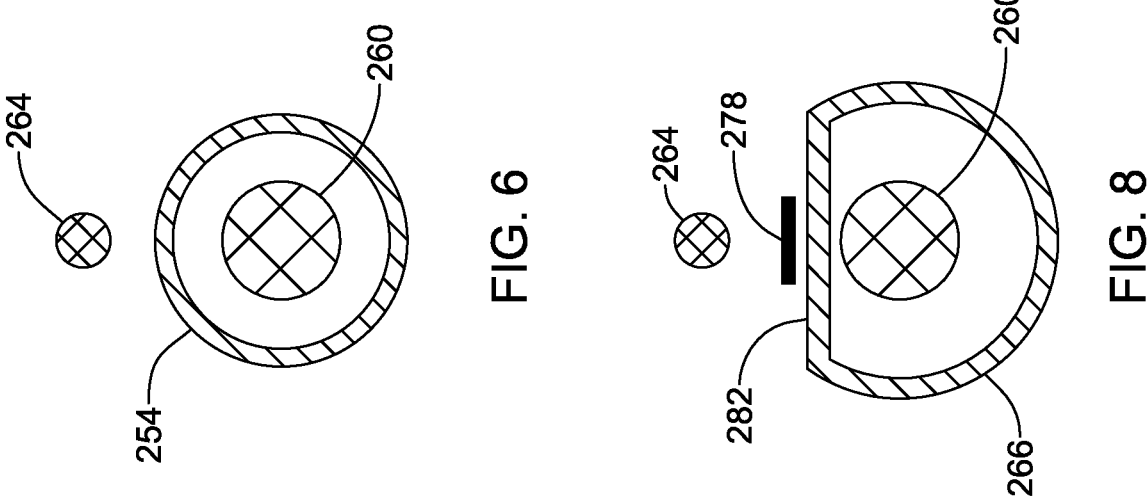
FIG. 8
FIG. 9

INTRAVASCULAR IMAGING DEVICES

CROSS-REFERENCE TO RELATED APPLICATIONS

This application claims the benefit of priority under 35 U.S.C. § 119 of U.S. Provisional Application No. 63/339,159, filed May 6, 2022, the entire disclosure of which is hereby incorporated by reference.

TECHNICAL FIELD

The present disclosure pertains to medical devices, and methods for manufacturing medical devices. More particularly, the present disclosure pertains to elongated intravascular imaging devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An intravascular imaging device is disclosed. The intravascular imaging device comprises: a catheter shaft assembly including a telescoping assembly and a catheter body; wherein the catheter body includes an imaging window and a distal end region having a first guidewire lumen formed therein; an imaging core disposed within the catheter shaft assembly; a distal shaft member disposed along an outer surface of the catheter body, the distal shaft member having a second guidewire lumen formed therein; and a rod having a first end region coupled to the distal shaft member and a second end region coupled to the telescoping assembly.

Alternatively or additionally to any of the embodiments above, the imaging core is translatable within the catheter shaft assembly.

Alternatively or additionally to any of the embodiments above, the imaging core includes an ultrasound transducer.

Alternatively or additionally to any of the embodiments above, the imaging core includes an optical coherence tomography imaging device.

Alternatively or additionally to any of the embodiments above, the telescoping assembly includes a first shaft coupled to a proximal end region of the catheter body and a second shaft coupled to the imaging core and movable relative to the first shaft.

Alternatively or additionally to any of the embodiments above, the second end region of the rod is coupled to the second shaft.

Alternatively or additionally to any of the embodiments above, the telescoping assembly includes an inner shaft coupled to the first shaft.

Alternatively or additionally to any of the embodiments above, the inner shaft defines a first lumen configured to receive the imaging core therein.

Alternatively or additionally to any of the embodiments above, the inner shaft defines a second lumen configured to receive the rod therein.

Alternatively or additionally to any of the embodiments above, the rod comprises a ribbon-shaped wire.

An intravascular imaging device is disclosed. The intravascular imaging device comprises: a catheter shaft including an imaging window and a distal end region; a telescoping shaft assembly coupled to the catheter shaft, the telescoping shaft assembly including an inner shaft, an intermediate shaft, and an outer shaft; wherein the inner shaft is coupled to the outer shaft; an imaging core disposed within the catheter shaft, the imaging core including a drive shaft and an ultrasound transducer coupled to the drive shaft; wherein the imaging core is coupled to the intermediate shaft; a distal shaft member disposed along an outer surface of the catheter shaft; wherein the distal shaft member has a first lumen configured to receive the imaging core and second lumen; and a rod having a first end region coupled to the distal shaft member and a second end region extending through the second lumen of the distal shaft member and coupled to the intermediate shaft.

Alternatively or additionally to any of the embodiments above, the distal end region includes a first guidewire lumen and the distal shaft member includes a second guidewire lumen axially aligned with the first guidewire lumen.

Alternatively or additionally to any of the embodiments above, the distal shaft member is configured to translate along the catheter shaft.

Alternatively or additionally to any of the embodiments above, the second lumen extends to a position that is proximal of a distal end of the distal shaft member.

Alternatively or additionally to any of the embodiments above, the rod comprises a ribbon-shaped wire.

Alternatively or additionally to any of the embodiments above, a hub is coupled to the imaging core.

Alternatively or additionally to any of the embodiments above, the intermediate shaft is coupled to the hub.

Alternatively or additionally to any of the embodiments above, the rod is coupled to the hub.

A method for imaging a blood vessel is disclosed. The method comprises: disposing an intravascular imaging device within a blood vessel, the intravascular imaging device comprising: a catheter shaft including an imaging window and a distal end region, a telescoping shaft assembly coupled to the catheter shaft, the telescoping shaft assembly including an inner shaft, an intermediate shaft, and an outer shaft, wherein the inner shaft is coupled to the outer shaft, an imaging core disposed within the catheter shaft, the imaging core including a drive shaft and an ultrasound transducer coupled to the drive shaft, wherein the imaging core is coupled to the intermediate shaft, a distal shaft member disposed along an outer surface of the catheter shaft, wherein the distal shaft member has a first lumen configured to receive the imaging core and second lumen, and a rod having a first end region coupled to the distal shaft member and a second end region extending through the second lumen of the distal shaft member and coupled to the intermediate shaft; and translating the imaging core relative to the catheter shaft.

Alternatively or additionally to any of the embodiments above, translating the imaging core relative to the catheter shaft includes translating the distal shaft member relative to the catheter shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 6 is a cross-sectional view taken through line 6-6 in FIG. 5.

FIG. 7 is a cross-sectional view taken through line 7-7 in FIG. 5.

FIG. 8 is a cross-sectional view taken through line 8-8 in FIG. 5.

FIG. 9 is a cross-sectional view taken through line 9-9 in FIG. 5.

Figure 1:
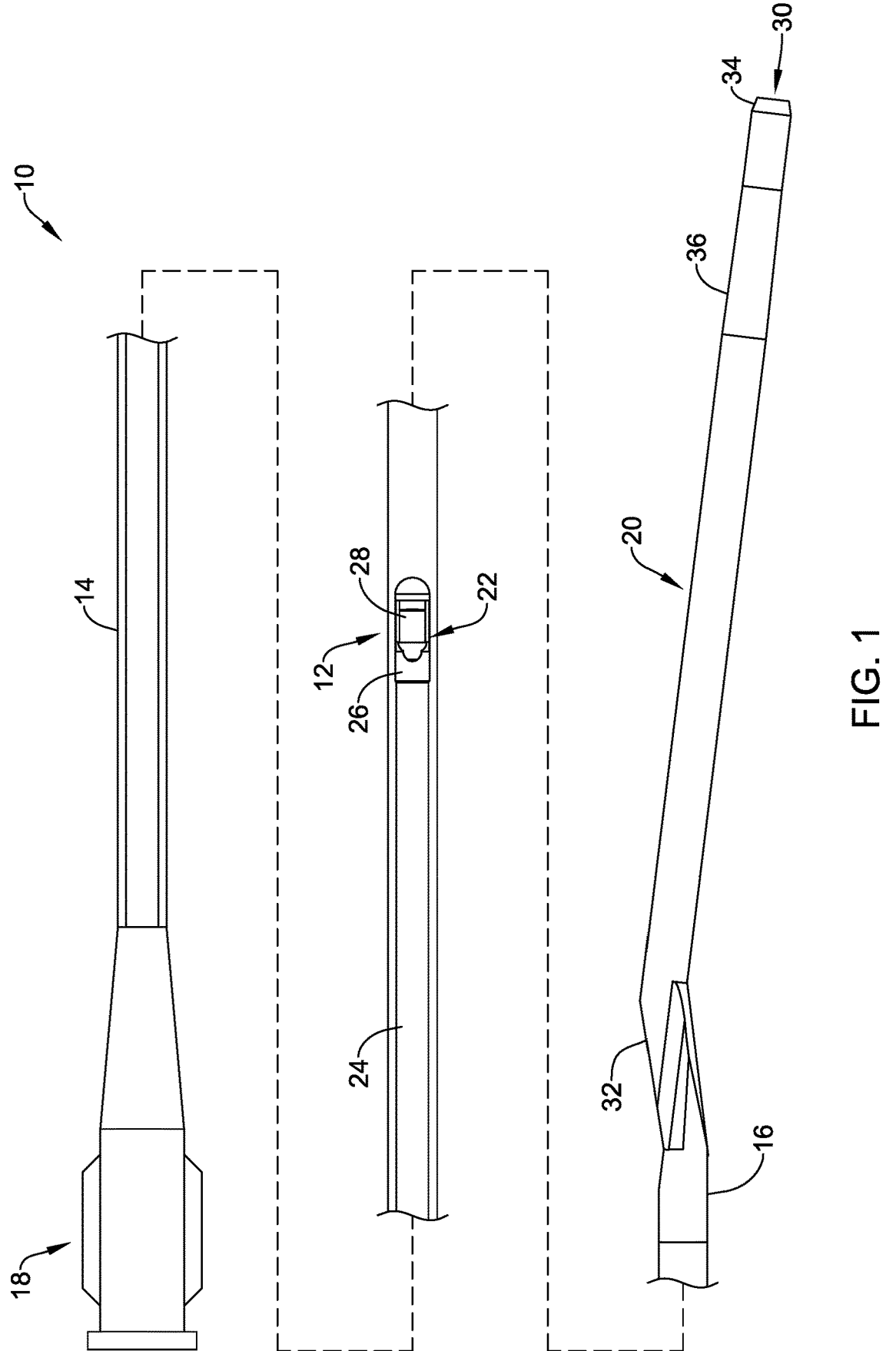
FIG. 1 is a side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a side view of an example medical device 10. In at least some instances, the medical device 10 takes the form of an imaging medical device. For example, the medical device 10 may be an intravascular ultrasound (IVUS) device that may be used to image a blood vessel. The structure/form of the medical device 10 can vary. In some instances, the medical device 10 may include an elongate shaft 12 having a proximal end region 14 and a distal end region 16. A proximal hub or connector 18 may be coupled to or otherwise disposed adjacent to the proximal end region 14. A tip member may be coupled to or otherwise disposed adjacent to the distal end region 16. The tip member 20 may include a guidewire lumen 30 having a guidewire exit port 32, an atraumatic distal end 34, one or more radiopaque markers 36, and/or other features. In some embodiments, the tip member 20 may extend at a non-parallel angle to the proximal end region 14 of the elongate shaft 12. An imaging assembly 22 may be disposed within a lumen of the shaft 12. In general, the imaging assembly may be used to capture/generate images of a blood vessel. In some instances, the medical device may include devices and/or features similar to those disclosed in U.S. Patent Application Pub. No. US 2012/0059241 and U.S. Patent Application Pub. No. US 2017/0164925, the entire disclosures of which are herein incorporated by reference. In at least some instances, the medical device 10 may resemble and/or include features that resemble the OPTICROSS™ Imaging Catheter, commercially available from BOSTON SCIENTIFIC, Marlborough, MA.

The imaging assembly 22 may include a drive cable or shaft 24, a housing 26, and an imaging member or transducer 28 coupled to the drive cable 24 and/or housing 26. In at least some instances, the transducer 28 includes an ultrasound transducer. Other transducers are also contemplated. The transducer 28 may be rotatable and/or axially translatable relative to the shaft 12. For example, the drive cable 24 may be rotated and/or translated in order to rotate and/or translate the transducer 28 (and the housing 26).

While not explicitly shown in FIG. 1, the medical device 10 may include a telescoping section, configured to allow the medical device operator to move the drive shaft 24 including the imaging assembly 22 proximally and distally within the catheter, without having to move the entire catheter within the patient. This allows the catheter operator to easily change the location of the imaging assembly or other medical device within the patient. For example, the telescoping section may be actuated to change the location of the imaging assembly 22 within the elongate shaft 12.

Further, when using the medical device 10, it may be desirable to prepare and/or flush the shaft 12. In order to flush the medical device 10, fluid may be infused at a flush port on or at the hub 18. The fluid may exit the medical device at a vent hole (not shown) adjacent to the distal end of the housing 26. In some instances, the flushing process may result in the formation of bubbles within the shaft 12. It may be desirable to flush the medical device 10 in a manner that reduces the formation of bubbles and/or removes/disrupts any bubbles that are formed because bubbles may reflect/disrupt a signal (e.g., an ultrasound signal) from the transducer 28, which disrupts the image. While flushing is generally effective for removing bubbles, some bubbles may still get caught within the shaft 12. Disclosed herein are medical devices that are designed to help reduce the formation of bubbles within the medical device.

Figure 2:
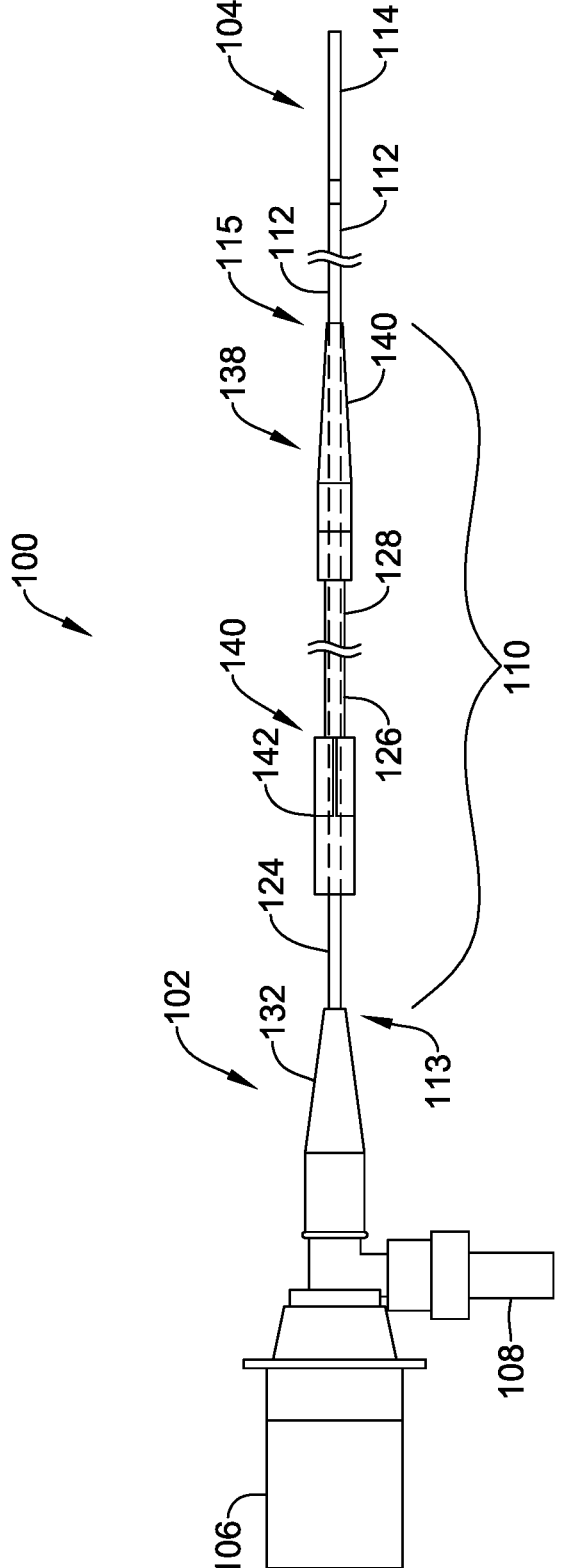
FIG. 2 is a side view of another illustrative medical device.

FIG. 2 illustrates a side view of another illustrative medical device, such as, but not limited to, a telescoping catheter 100. The catheter 100 extends from a proximal end region 102 to a distal end region 104. A proximal hub 106 may be affixed adjacent to the proximal end region 102. The proximal hub 106 may include a check valve and flush port 108. In order to flush the catheter 100, fluid may be infused at the flush port 108. The catheter 100 may further include a telescoping section 110 extending from a proximal end region 113 to a distal end region 115 and positioned between the proximal end region 102 and the distal end region 104 of the catheter 100. An elongate shaft 112 extends distally from the distal end region 115 of the telescoping section 110. The elongate shaft 112 may include a tip member 114 adjacent the distal end region 104 of the catheter 100. The tip member 114 may be similar in form and function to the tip member 20 described with respect to FIG. 1. For example, the tip member 114 may include a guidewire lumen having a guidewire exit port, an atraumatic distal end, one or more radiopaque markers, and/or other features.

An imaging assembly 116 (see, for example, FIG. 3) may be movably positioned within a lumen of the elongate shaft 112. The imaging assembly 116 may include a drive cable or shaft 120, a housing 122, and an imaging member or transducer 118 coupled to the drive cable 120 and/or housing 122. It is contemplated that the imaging assembly 116 may include or be replaced with another medical device, such as, but not limited to, a cutting head, or other device. The particular device chosen for the drive cable 120 may be selected based on the desired function for the catheter 100. The drive cable 120 may extend proximally from the imaging member 118 through the telescoping section 110 to the proximal hub 106. The proximal hub 106 may contain components adapted to interface the drive cable 120 with a power source and/or other electronic couplings. In some cases, a proximal end of the drive cable 120 may be affixed to the proximal hub 106. While not explicitly shown, the drive cable 120 may include a single layer outer jacket or coating or a two-layer outer jacket or coating, as desired. If so provided, the outer jacket may extend a full length of the drive cable 120 or less than a full length of the drive cable 120.

The telescoping section 110 may include a first or intermediate sheath 124, a second or outer sheath 126, and a third or inner sheath 128. Generally, the outer sheath 126 may be disposed over the intermediate sheath 124 and the intermediate sheath 124 disposed over the inner sheath 128. The intermediate sheath 124 may be axially and/or rotatably displaced relative to the outer and inner sheaths 126, 128 such that movement of the proximal hub 106 is translated to movement of the intermediate sheath 124 and the drive cable 120. A distal hub 138 may be positioned adjacent the distal end region 115 of the telescoping section 110. The distal hub 138 may include a distal strain relief 139 configured to be coupled to the elongate shaft 112. Further, the distal ends of the outer sheath 126 and the inner sheath 128 may each be fixedly secured to the distal hub 138.

The intermediate sheath 124 extends distally from a proximal end region 130 coupled to a proximal strain relief 132 to a distal end 134 extending within the outer sheath 126. The intermediate sheath 124 may have a constant diameter from the proximal end region 130 to the distal end 134, although this is not required. The proximal strain relief 132 is coupled to the proximal hub 106. The intermediate sheath 124 is movable relative to the inner and outer sheaths 128, 126 such that the distal end 134 of the intermediate sheath 124 is movable between the distal hub 138 and a housing 142. The intermediate sheath 124 defines a lumen extending from the proximal end region 130 to the distal end 134 thereof. The lumen may receive and/or house a portion of the drive shaft 120 and/or the inner sheath 128.

The outer sheath 126 extends distally from a housing or receptacle 142 to a distal end (e.g., which may be affixed to the distal hub 138). The outer sheath 126 defines a lumen extending from the proximal end region to the distal end. The lumen may receive or house a portion of the inner sheath 128 and/or the intermediate sheath 124.

The inner sheath 128 extends distally from a proximal end region to a distal end affixed to the distal hub. The inner sheath 128 defines a lumen extending from the proximal end region to the distal end. The lumen may receive or house a portion of the drive shaft 120. For example, the inner sheath 128 may be configured to support the drive shaft 120 when the intermediate sheath 124 is in a proximally displaced configuration (see, for example, FIG. 4). In some embodiments, the proximal end region of the inner sheath 128 may be positioned adjacent to the proximal end region of the outer sheath 126. In other embodiments, the proximal end region of the inner sheath 128 may be distal to the proximal end region of the outer sheath 126.

Figure 3:
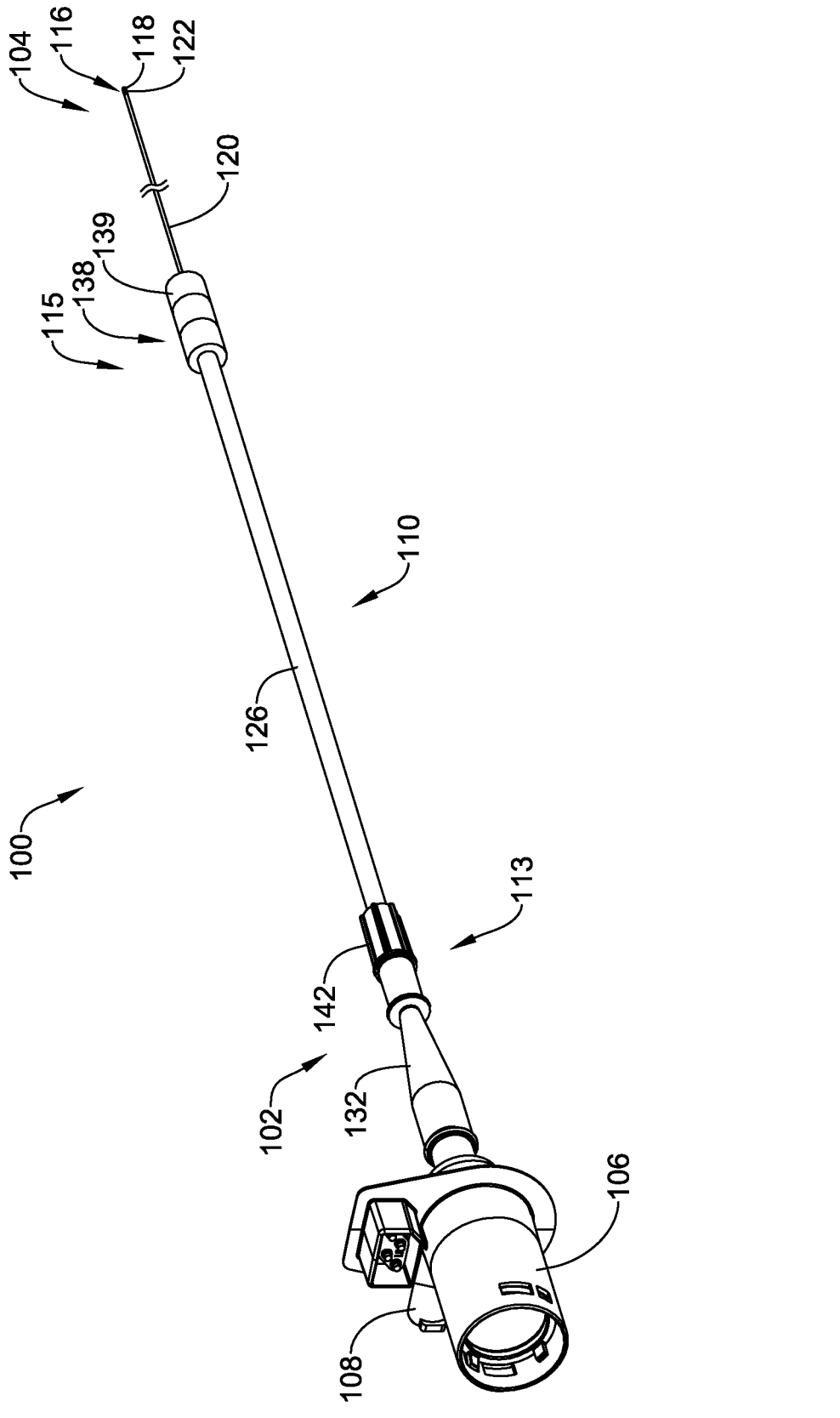
FIG. 3 is a perspective view of the medical device of FIG. 2 in a retracted configuration.

FIG. 3 illustrates a perspective view of the telescoping catheter of FIG. 2 with the proximal hub 106 and the intermediate sheath 124 (and hence the drive shaft 120) in a distalmost position. This configuration may be considered to be fully retracted, as the catheter 100 has the shortest length. In FIG. 3, the elongate shaft 112 is not shown to more clearly show the structure of the imaging assembly 116. In the embodiment of FIG. 3, the intermediate sheath 124 has been distally advanced within the lumen of the outer sheath 126. Distal movement of the intermediate sheath 124 may be limited by a mechanical stop created between the proximal strain relief 132 and the housing 142. When the proximal hub 106 and the intermediate sheath 124 are in a distalmost position, a majority of the length of the lumen 136 of the intermediate sheath 124 may surround the inner sheath 128.

Figure 4:
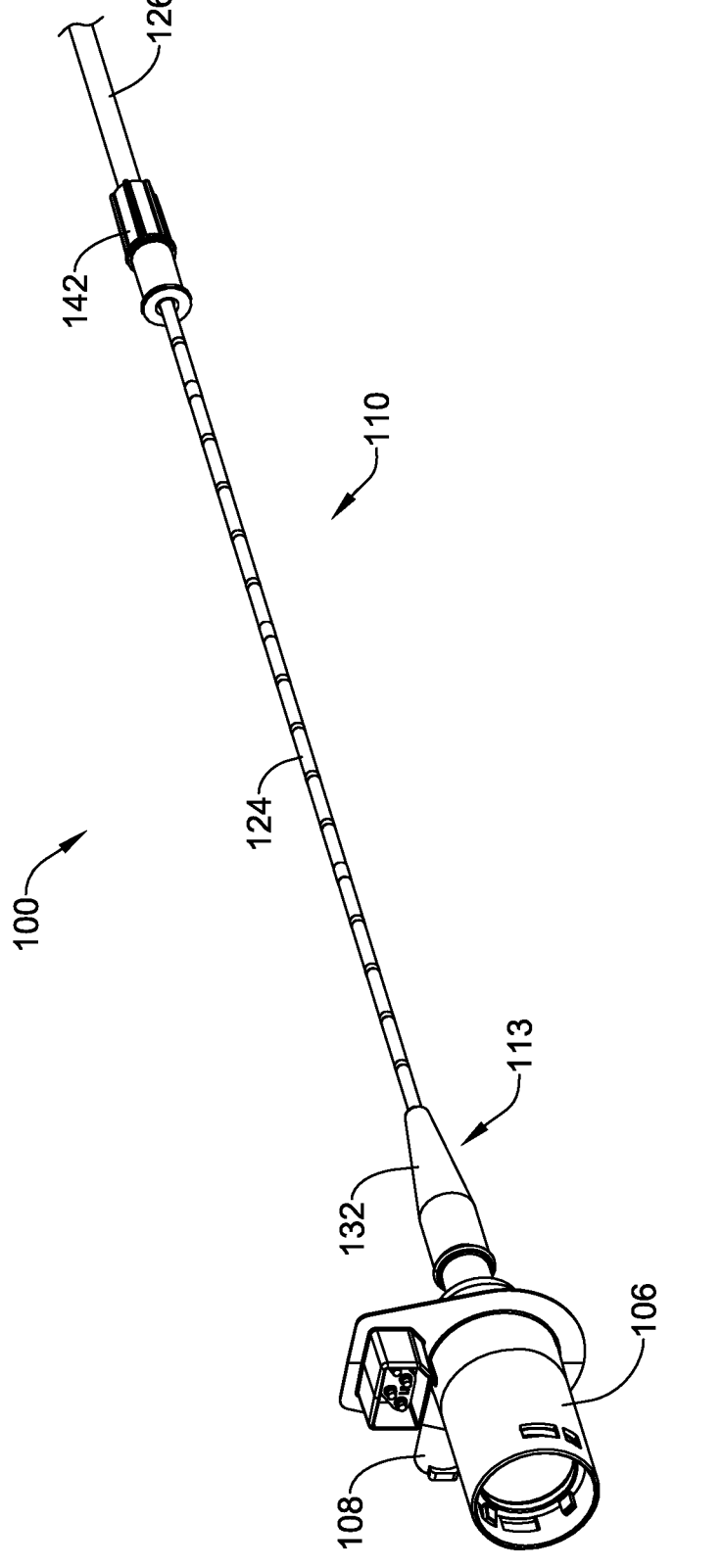
FIG. 4 is a perspective view of the medical device of FIG. 2 in an extended configuration.

FIG. 4 illustrates a perspective view of a proximal portion of the telescoping catheter of FIG. 2 with the proximal hub 106 and the intermediate sheath 124 (and hence the drive shaft 120) near a proximal most position. This configuration may be considered to be fully extended, as the catheter 100 has the greatest length. In the embodiment of FIG. 4, the intermediate sheath 124 has been proximally displaced within the lumen of the outer sheath 126. Proximal movement of the intermediate sheath 124 may be limited by a mechanical stop created between mating features on a distal end region of the intermediate sheath 124 and the housing 142. When the proximal hub 106 and the intermediate sheath 124 are in a proximal most position, a majority of the length of the lumen 136 of the intermediate sheath 124 may surround the drive cable 120.

While FIGS. 3 and 4 illustrate the approximate extremes of the movement of the telescoping section 110, the proximal hub 106 and the intermediate sheath 124 may be positioned at any location between. As the drive cable 120 is coupled to the proximal hub 106, proximal and distal movement is translated to the drive cable 120 and the imaging assembly 116 to allow the imaging assembly to move without moving the entire catheter 100. It is further contemplated that rotational movement of the proximal hub 106 will also be translated to the drive shaft 120 and imaging assembly 116 to allow for rotation of the imaging assembly 116 within the elongate shaft 112.

During a coronary intervention, an imaging device may be navigated through the tortuous anatomy. When doing so, it is possible that the imaging device may kink or otherwise deform in a way that may disrupt the function of the device. Disclosed herein are intravascular imaging devices that include structural features to the device and that, for example, may help to reduce kinking as well as provide additional desirable benefits.

Figure 5:
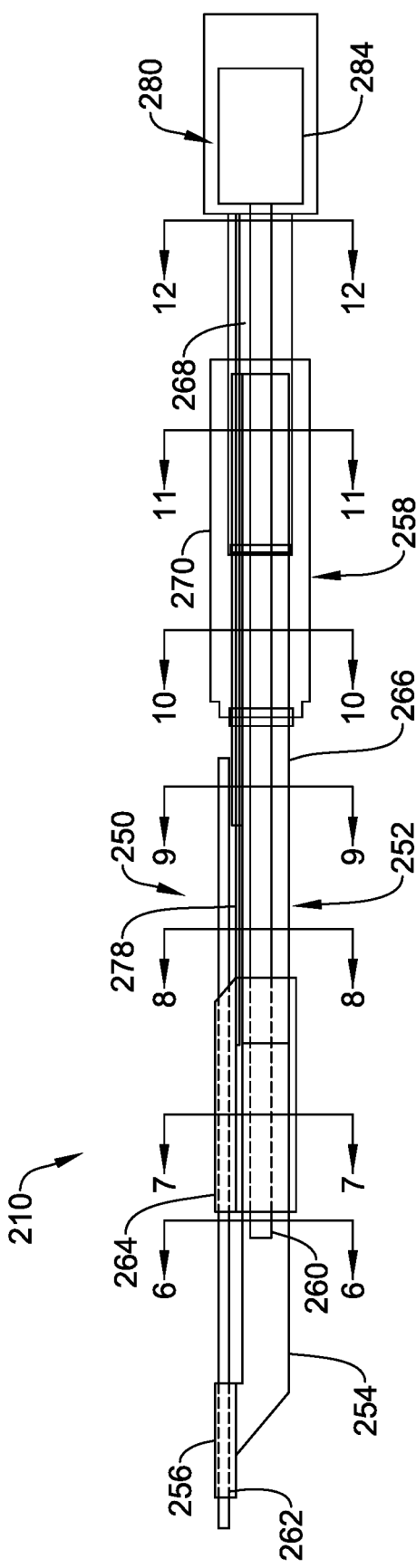
FIG. 5 is a cross-sectional view taken through line 5-5 in FIG. 5.

FIG. 5 is a side view of a portion of an example intravascular imaging device 210 that may be similar in form and function to other intravascular imaging devices disclosed herein. The intravascular imaging device 210 may include a catheter assembly 250. The catheter assembly 250 may include a shaft or catheter body 252, an imaging window 254, a distal end region 256, and a telescoping assembly 258. An imaging core 260 may extend through the catheter body 252. The imaging core 260 may include an ultrasound transducer, an optical coherence tomography imaging device, a combination thereof, and/or the like. The imaging core 260 may be used in a manner similar to what is disclosed herein to image a blood vessel. The distal end region 256 may define a guidewire lumen 262 that is configured to have a guidewire 264 extend therethrough.

A number of arrangements and/or configurations are contemplated for the catheter assembly 250. For example, in some instances the telescoping assembly 258 is disposed at or near the proximal end of the catheter assembly 250. The catheter body 252 may be a region of the catheter assembly 250 generally disposed distally of the telescoping assembly 258. In some instances, the imaging window 254 and/or the distal end region 256 may be considered to be part(s) of the catheter body 252. In other instances, the imaging window 254 and/or the distal end region 256 may be separate portion(s)/region(s) of the catheter assembly 250 that are disposed distally of and attached to the catheter body 252.

The telescoping assembly 258 may include an inner shaft 266, an intermediate shaft 268, and an outer shaft 270. In some instances, the inner shaft 266 may be axially fixed relative to the outer shaft 270. In other words, the inner shaft 266 may be configured so that the inner shaft 266 does not move relative to the outer shaft 270. The intermediate shaft 268 may be slidable (e.g., translatable) relative to the inner shaft 266 and the outer shaft 270. In at least some instances, the intermediate shaft 268 may be axially fixed relative to the imaging core 260. In other words, the intermediate shaft 268 may be configured so that movement of the intermediate shaft 268 results in corresponding movement of the imaging core 260. Because the intermediate shaft 268 may be slidable relative to the inner shaft 266 and the outer shaft 270, and because the intermediate shaft 268 maybe axially fixed relative to the imaging core 260, movement of the intermediate shaft 268 shifts (e.g., translates) the intermediate shaft 268 and the imaging core 260 relative to the inner shaft 266 and the outer shaft 270.

A distal shaft member 272 may be disposed along the catheter assembly 250. The distal shaft member 272 may take the form of a sleeve or sheath that is disposed about the catheter body 252. In some instances, the distal shaft member 272 may be disposed adjacent to the distal end region 256 of the catheter assembly 250. A rod 278 may be coupled to the distal shaft member 272. The rod 278 may be configured to couple the distal shaft member 272 to the intermediate shaft 268 and/or the imaging core 260 as will be explained in more detail herein.

The distal shaft member 272 and rod 278 may provide a number of desirable features to the intravascular imaging device 210. For example, the distal shaft member 272 may provide additional bulk and/or structural support that may help a clinician be able to more efficiently advance the intravascular imaging device 210 toward a target and/or help to reduce kinking. In some instances, the distal shaft member 272 may include a guidewire lumen (e.g., the guidewire lumen 276 as shown in FIG. 7) that can help provide additional structural support to the intravascular imaging device 210 while tracking over a guidewire. In at least some instances, the rod 278 may be sufficiently stiff so as to enhance or otherwise aid in providing structural support. The rod 278 may take the form of a wire (e.g., round in cross-section, non-circular in cross-section, polygonal shaped in cross-section, ribbon-shaped, and/or the like) that helps to hold support the distal shaft member 272. The rod 278 may extend to the proximal end of the catheter assembly 250.

It can be appreciated that when the distal shaft member 272 is disposed adjacent to the distal end region 256 of the catheter assembly 250, the distal shaft member 272 could block or obscure the imaging core 260, for example if the imaging core 260 is translated (e.g., during a pullback procedure). Because of this, it may be desirable for the distal shaft member 272 to move (e.g., translate) together with the imaging core 260. For example, in some instances, the imaging core 260 may extend to a position that is distal of the distal shaft member 272. During a translation procedure (e.g., a pullback procedure), the distal shaft member 272 may be configured to move along with the imaging core 260 and maintain its arrangement so the distal end of the imaging core 260 maintains its position distal of the distal shaft member 272. Thus, if the imaging core 260 is proximally retracted, the distal shaft member 272 retracts along with the imaging core 260. This helps to prevent the distal shaft member 272 from blocking or obscuring the imaging core 260.

A hub 280 may be disposed at the proximal end of the catheter assembly 250. The intermediate shaft 268 may be coupled to the hub 280. In some of these and in other instances, the rod 278 may be coupled to the hub 280. In some of these and in other instances, the imaging core 260 may be coupled to the hub 280. The hub 280 may be used to shift (e.g., translate) the intermediate shaft 268, the distal shaft member 272, the rod 278, and the imaging core 260 relative to the inner shaft 266 and the outer shaft 270. The hub 280 may include an imaging core rotating device 284. The imaging core rotating device 284 may be used to rotate the imaging core 260 during an imaging procedure. In some instances, the hub 280 may include a translating device or "pullback" device that is configured to translate the imaging core 260 (as well as the intermediate shaft 268 and the rod 278) relative to the inner shaft 266 and the outer shaft 270.

Some of the various structures and/or arrangements of the structures of the catheter assembly 250 can be more clearly seen in FIGS. 6-12. For example, FIG. 6 illustrates a distal portion of the catheter assembly 250. Here is can be seen that the imaging core 260 may be disposed within the imaging window 254. The imaging window 254 may be formed from a material that is substantially transparent to the energy utilized for imaging. For example, the imaging window 254 may be transparent to acoustic or ultrasound energy when an ultrasound transducer is used for imaging. The guidewire 264 can be seen along the exterior of the imaging window 254.

FIG. 7 illustrates a portion of the catheter assembly 250 that is proximal of the portion shown in FIG. 6. Here it can be seen that the distal shaft member 272 may be disposed over the imaging window 254. In some instances, the distal shaft member 272 a guidewire portion 274 defining a guidewire lumen 276. This may allow the distal shaft member 272 to tracked along the guidewire 264 during an imaging procedure.

Turning now to FIG. 8, here it can be seen that the imaging core 260 may be disposed within the inner shaft. In addition, the inner shaft 266 be cut/slit, skived, or otherwise manufactured to have a flattened region 282 where the rod 278 extends along the exterior of the inner shaft 266 as shown in FIG. 8. The flattened region 282 may also be described as a portion of the inner shaft 266 (e.g., a portion having a secondary lumen) is removed from the inner shaft 266. The inner shaft 266 may then transition along its length to a multi-lumen region or section. For example, a more proximal region of the inner shaft 266 may include a secondary lumen region 286 defining a secondary lumen 288. The rod 278 may extend within the secondary lumen 288 as shown in FIG. 9.

Figures 10, 11, 12:
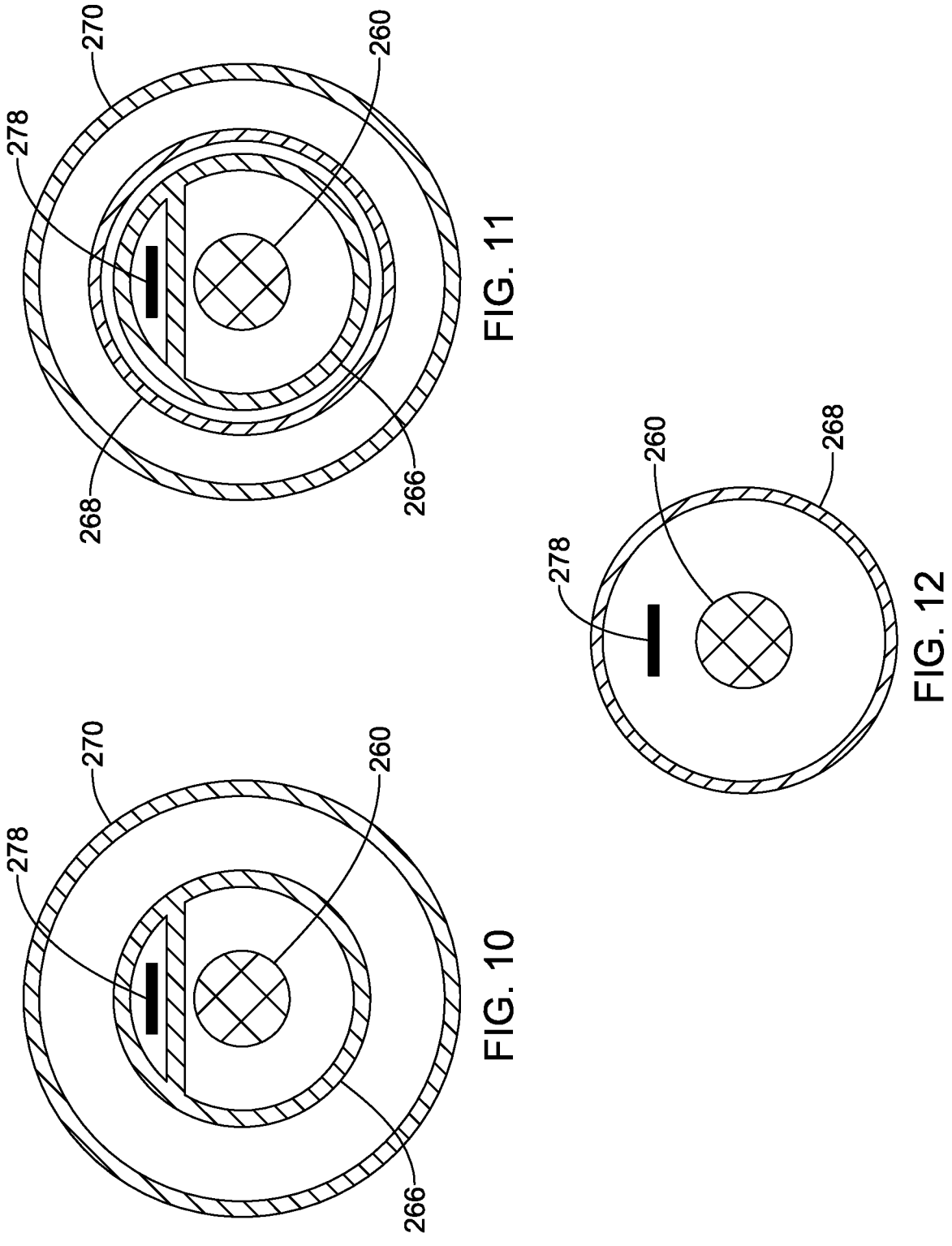
FIG. 10 is a cross-sectional view taken through line 10-10 in FIG. 5.
FIG. 11 is a cross-sectional view taken through line 11-11 in FIG. 5.
FIG. 12 is a cross-sectional view taken through line 12-12 in FIG. 5.

Moving proximally along the catheter assembly 250, the inner shaft 266 may extend within the outer shaft 270 as shown in FIG. 10. Further proximally, the intermediate shaft 268 may be disposed between the inner shaft 266 and the outer shaft 270 as shown in FIG. 11. Finally, at a position near the proximal end of the catheter assembly 250, the intermediate shaft 268 may be disposed about the imaging core 260 as shown in FIG. 12. At the proximal end of the catheter assembly 250 the imaging core 260, the intermediate shaft 268, and the rod 278 may be coupled to one another, for example by coupled each to the hub 280.

Figure 13:
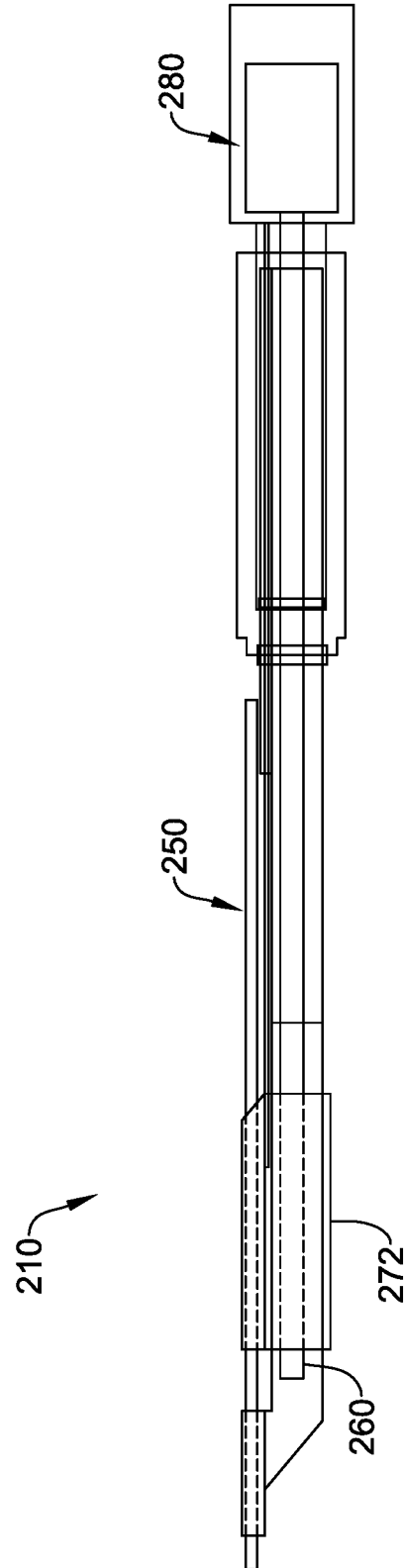
FIG. 13 is a side view of a portion of an example intravascular imaging device.
Figure 14:
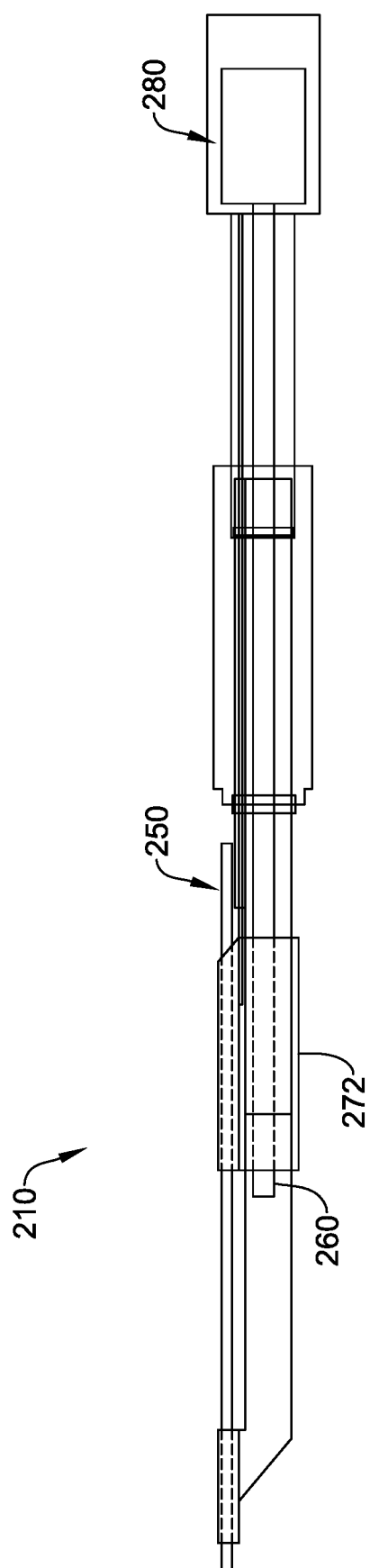
FIG. 14 is a side view of a portion of an example intravascular imaging device.

FIGS. 13-14 schematically illustrate a portion of an imaging procedure. In such a procedure, the imaging core 260 may be translated along the catheter assembly 250 (e.g., during a pullback procedure). When doing so, the hub 280 may be translated (e.g., while holding steady the inner shaft 266 and the outer shaft 270), which results in the imaging core 260 moving within the catheter assembly 250. Because it may be desirable to avoid having the distal shaft member 272 block or otherwise obscure the imaging core 260, the distal shaft member 272 may translate along the catheter assembly 250 as shown in FIG. 14 along with the imaging core 260 (and along with the intermediate shaft 268).

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An intravascular imaging device, comprising:
a catheter shaft assembly including a telescoping assembly and a catheter body;
wherein the telescoping assembly including an inner shaft, an outer shaft, and intermediate shaft disposed between the inner shaft and the outer shaft;
wherein the intermediate shaft is configured to be movable relative the inner shaft and the outer shaft;
wherein the catheter body includes an imaging window and a distal end region having a first guidewire lumen formed therein;
an imaging core disposed within the catheter shaft assembly;
wherein the imaging core is coupled to the intermediate shaft;
a distal shaft member disposed along an outer surface of the catheter body, the distal shaft member having a second guidewire lumen formed therein; and
a rod having a first end region coupled to the distal shaft member and a second end region coupled to the intermediate shaft such that the rod, the distal shaft member, the intermediate shaft, and the imaging core move together relative to the catheter body.

2. The intravascular imaging device of claim 1, wherein the imaging core is translatable within the catheter shaft assembly.

3. The intravascular imaging device of claim 1, wherein the imaging core includes an ultrasound transducer.

4. The intravascular imaging device of claim 1, wherein the imaging core includes an optical coherence tomography imaging device.

5. The intravascular imaging device of claim 1, wherein the inner shaft defines a first lumen configured to receive the imaging core therein.

6. The intravascular imaging device of claim 5, wherein the inner shaft defines a second lumen configured to receive the rod therein.

7. The intravascular imaging device of claim 1, wherein the rod comprises a ribbon-shaped wire.

8. An intravascular imaging device, comprising:
a catheter shaft including an imaging window and a distal end region;
a telescoping shaft assembly coupled to the catheter shaft, the telescoping shaft assembly including an inner shaft, an outer shaft, and an intermediate shaft disposed between the inner shaft and the outer shaft;
wherein the inner shaft is coupled to the outer shaft;
an imaging core disposed within the catheter shaft, the imaging core including a drive shaft and an ultrasound transducer coupled to the drive shaft;
wherein the imaging core is coupled to the intermediate shaft;
a distal shaft member disposed along an outer surface of the catheter shaft;
wherein the distal shaft member has a first lumen configured to receive the imaging core and second lumen; and
a rod having a first end region coupled to the distal shaft member and a second end region extending through the second lumen of the distal shaft member and coupled to the intermediate shaft such that translation of the distal shaft member results in translation of the intermediate shaft and the imaging core relative to the catheter shaft.

9. The intravascular imaging device of claim 8, wherein the distal end region includes a first guidewire lumen and the distal shaft member includes a second guidewire lumen axially aligned with the first guidewire lumen.

10. The intravascular imaging device of claim 8, wherein the distal shaft member is configured to translate along the catheter shaft.

11. The intravascular imaging device of claim 8, wherein the second lumen extends to a position that is proximal of a distal end of the distal shaft member.

12. The intravascular imaging device of claim 8, wherein the rod comprises a ribbon-shaped wire.

13. The intravascular imaging device of claim 8, wherein a hub is coupled to the imaging core.

14. The intravascular imaging device of claim 13, wherein the intermediate shaft is coupled to the hub.

15. The intravascular imaging device of claim 13, wherein the rod is coupled to the hub.

16. A method for imaging a blood vessel, the method comprising:

disposing an intravascular imaging device within a blood vessel, the intravascular imaging device comprising:

a catheter shaft including an imaging window and a distal end region, a telescoping shaft assembly coupled to the catheter shaft, the telescoping shaft assembly including an inner shaft, an outer shaft, and an intermediate shaft disposed between the inner shaft and the outer shaft, wherein the inner shaft is coupled to the outer shaft, an imaging core disposed within the catheter shaft, the imaging core including a drive shaft and an ultrasound transducer coupled to the drive shaft, wherein the imaging core is coupled to the intermediate shaft, a distal shaft member disposed along an outer surface of the catheter shaft, wherein the distal shaft member has a first lumen configured to receive the imaging core and second lumen, and a rod having a first end region coupled to the distal shaft member and a second end region extending through the second lumen of the distal shaft member and coupled to the intermediate shaft; and translating the imaging core relative to the catheter shaft by translating the rod relative to the catheter shaft.

17. The method of claim 16, wherein translating the imaging core relative to the catheter shaft includes translating the distal shaft member relative to the catheter shaft.

* * * * *